(12) United States Patent
Giordano

(10) Patent No.: US 6,881,488 B2
(45) Date of Patent: *Apr. 19, 2005

(54) METHOD FOR FABRICATING ENDODONTIC, ORTHODONTIC, AND DIRECT RESTORATIONS HAVING INFUSED CERAMIC NETWORK

(75) Inventor: Russell A. Giordano, Marlborough, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/177,430

(22) Filed: Jun. 21, 2002

(65) Prior Publication Data

US 2002/0162482 A1 Nov. 7, 2002

Related U.S. Application Data

(63) Continuation of application No. 09/448,050, filed on Nov. 23, 1999, now abandoned, which is a division of application No. 09/201,455, filed on Nov. 30, 1998, now Pat. No. 6,159,417, which is a continuation-in-part of application No. 08/854,805, filed on May 12, 1997, now Pat. No. 5,843,348, which is a continuation of application No. 08/307,455, filed on Sep. 19, 1994, now abandoned.

(51) Int. Cl.[7] .............................................. A61K 6/06
(52) U.S. Cl. ...................... 428/432; 428/426; 428/428; 428/446; 428/451
(58) Field of Search ..................... 433/222.1, 212.1; 623/23.56, 23.58, 23.53; 428/432, 426, 428, 446, 451

(56) References Cited

U.S. PATENT DOCUMENTS

| | | | |
|---|---|---|---|
| 3,250,833 A | 5/1966 | Wagner | 264/628 |
| 3,423,828 A | 1/1969 | Halpern | |
| 3,713,860 A | 1/1973 | Auskern | 117/8.5 |
| 4,381,918 A | 5/1983 | Ehrnford | |
| 4,772,436 A | 9/1988 | Tyszblat | 264/19 |
| 4,777,153 A | 10/1988 | Sonuparlak et al. | 501/82 |
| 5,164,233 A | 11/1992 | Sonuparlak et al. | 427/399 |
| 5,221,558 A | 6/1993 | Sonuparlak et al. | 427/376.1 |
| 5,427,722 A | 6/1995 | Fouts et al. | 264/87 |
| 5,676,745 A | 10/1997 | Kelly et al. | 106/35 |
| 5,843,348 A * | 12/1998 | Giordano | 264/19 |
| 6,159,417 A * | 12/2000 | Giordano | 264/628 |
| 6,271,282 B1 * | 8/2001 | Giordano | 523/116 |

FOREIGN PATENT DOCUMENTS

| | | |
|---|---|---|
| EP | 0 701 808 | 3/1996 |
| EP | 0 803 241 | 10/1997 |

OTHER PUBLICATIONS

"Mechanical Properties of 2–D Nicalon Fiber–Reinforced LANXIDE Aluminum Oxide and Aluminum Nitride Matrix Composites," Fareed et al. *Ceram. Eng. Sci. Proc.* 1990. vol. 11.

"Tailoring the Microstructure of Ceramics and Ceramis Matrix Composites Through Processing," B. Sonuparlak. *Composites Science and Technology.* 1990. vol. 37.

* cited by examiner

*Primary Examiner*—C. Melissa Koslow
(74) *Attorney, Agent, or Firm*—Gauthier & Connors LLP

(57) ABSTRACT

A ceramic network for endodontic, orthodontic or restorative materials infused with a monomer, glass or metal alloy. After infusion of the monomer, glass or metal alloy, the monomer, glass or metal alloy is treated to form with the ceramic network an interpenetrating network of improved wear, resistance and flexibility.

6 Claims, 2 Drawing Sheets

METHOD FOR FABRICATING ENDODONTIC, ORTHODONTIC, AND DIRECT RESTORATIONS HAVING INFUSED CERAMIC NETWORK

CROSS REFERENCES TO RELATED APPLICATIONS

This application is a CON of U.S. patent application Ser. No. 09/448,050 filed on Nov. 23, 1999, now abandoned, which is a DIV of U.S. patent application Ser. No. 09/201,455 filed on Nov. 30, 1998, now U.S. Pat. No. 6,159,417, which is a CIP of U.S. patent application Ser. No. 08/854,805 filed on May 12, 1997, now U.S. Pat. No. 5,843,348, which is a CON of U.S. patent application Ser. No. 08/307,455 filed on Sep. 19, 1994, now abandoned.

BACKGROUND OF THE INVENTION

1. Field of the Invention

The invention relates to ceramic network materials used for restorative material and for various devices such as posts, implant abutments, orthodontic brackets, or blocks.

2. Description of Related Art

Referring to FIG. 1, natural tooth enamel 10 is a hard, vitreous substance that covers the outer portions on a tooth crown 1. Hardness is an important enamel property because enamel 10 provides a protective covering for the softer underlying dentin 12. Enamel 10 also serves as a masticatory surface on which food is crushed, ground, and chewed. Specifically, hardness is a measure of the ability of tooth enamel to withstand deformation by indentation or scraping, or the like, and mature enamel demonstrates a Knoop hardness number (KHN, i.e., the ratio of a given load to an area of indentation expressed in Kg/mm$^2$) in a range of about 200 to 500 KHN.

Because enamel is semitranslucent, the color of enamel depends in part upon its thickness. For this reason, enamel may assume the various colors of its underlying structures. Thus, when enamel is thicker, and consequently more opaque, it may appear grayish or bluish white reflecting more of its inherent coloration. When enamel is relatively thin, however, it may be yellow-white in appearance, reflecting the underlying generally-yellowish dentin.

As demonstrated by FIG. 1, dentin 12 may constitute the largest single component of tooth structure, extending almost the entire length of the tooth. Dentin 12 is covered by enamel 10 on the crown 1 and by cementum 14 on the root. The internal surface of dentin 12 forms the walls of a pulp cavity 16 which primarily contains pulpal tissue 18. Further, the walls of pulp cavity 16 may closely conform to the outline of the external surface of the dentin 12.

Dentin and bone in general are natural ceramic-composites. Chemically, dentin 12 is composed of organic and inorganic matter. As noted above, the inorganic matter includes calcium phosphate in the form of hydroxyapatite ($Ca_{10}(PO_4)_6(OH_2)$). The organic matter is primarily collagenous material. The hydroxyapatite crystals are bonded to themselves to create tubules through which collagen fibers run and these may be attached to the dentin.

Restorative materials generally are tested on three criteria: sufficient hardness, adequate fit, and acceptable aesthetics, e.g., color match. Of these three, however, aesthetics often are the deciding factor in the choice of restorative materials. Composite resins and ceramics are in widespread use due in part to their ability to match the color of a patient's natural teeth. Composite resins may be composed of a glass in a polymer matrix. This combination, however, may result in rapid wear of the restoration, as the softer polymer is lost, and the glass filler pulls out of the remaining polymer. High wear rates are associated with rapid loss of restorative strength. Restorative ceramics may also be problematic. Despite relatively high strength and hardness, ceramic materials also are generally brittle, such that they may withstand only minimal deformation without failing. Thus, wear in current composite resin materials and catastrophic fracture of ceramic restorations are significant limitations of currently available restorative materials.

On the other hand, direct filling composite resin restorations are widely used to fill decayed teeth. These materials consist of a glass and/or ceramic particles placed into a resin to create a paste. The paste is placed directly into the tooth and cured.

Orthodontics involves movement of teeth by applying force to the teeth via wires which are tied to brackets mounted on the teeth. Most brackets are fabricated from metal which is not aesthetic. New brackets fabricated from alumina are more aesthetic but tend to fracture prematurely and also wear the opposing teeth. Alumina brackets also have high friction with the archwires which slows the tooth movement and prolongs treatment time. Plastic brackets deform and thus decrease the force transmitted to the teeth, prolonging treatment.

SUMMARY OF THE INVENTION

A process for preparing a ceramic network for fabricating stronger, more aesthetic, and better wearing restorative materials. A restorative material may be based on monomer, glass, or metal infusion or a ceramic network, or monomer infusion of a partially, glass infused ceramic network may present advantages over currently available restorations, such as composite resin and ceramic restorations, with respect to wear resistance and strength. It is a technical advantage that such a restorative material may have improved wear resistance and flexibility with respect to conventional composite resins and ceramics. It is a further technical advantage that in restorative materials made according to this invention, the masticatory surface, e.g., the coronal portion, may be glass infused to provide a bard, wear resistant restoration. For example, a glass layer may have a hardness in a range of about 300 to 600 KHN and an elastic modulus in a range of about 70 to 80 GPa. In addition, it may have a flexural strength of about 200–500 MPa, and the polymer infused interior may have a flexural strength of about 150–80 MPa and an elastic modulus of 15–25 GPa.

One embodiment of the invention includes producing implant abutment parts which may be machined directly from resin infused ceramic or the ceramic mixed with a binder which may be directly molded to form the part. The binder is burned out and the ceramic is sintered, infused and then cured.

Additionally, endodontically treated teeth often require crown restorations. Polymer infused ceramic may be used to fabricate posts, or post and cores may be milled directly from a block or can be molded into custom or prefabricated parts. Advantages of this material include its increased strength, improved translucency and cementing ability.

Furthermore, orthodontic brackets which are polymer infused have the advantages of improved fracture toughness, aesthetics and decreased enamel wear. They also have decreased friction with orthodontic arch wires which eases tooth movement and decreases treatment time. These brackets may be fabricated by machining a block of polymer infused ceramic or by pressing the powder/powder plus binder into a mold. The binder is burned out and the ceramic is sintered. The ceramic is then infused with a polymer.

Yet another embodiment involves direct filling composite resin restorations which are widely used to fill decayed teeth. These materials consist of a glass and/or ceramic particles placed into a polymer to create a paste. The paste is placed directly into the tooth and cured. An application of this technology involves fabricating blocks of polymer infused ceramics and then grinding these blocks into a powder, the powder is then mixed with a polymer to form a paste which can be inserted into the tooth and cured. The advantage of this process is that the filler material contains ceramic particles which are joined, whereas all of the particles in a conventional composite polymer are unjoined. The latter creates increased wear of the polymer as the particles pull out of the polymer. In this formulation bonding of the filler particles should be enhanced because there are interconnected ceramic particles already partially filled within the polymer. Filler pull out is more difficult resulting in decreased wear.

Other objects, advantages, and features will be apparent when the detailed description of the invention and the drawings are considered.

BRIEF DESCRIPTION OF THE DRAWINGS

For a more complete understanding of the present invention and the technical advantages thereof, reference is made to the following description taken in conjunction with accompanying drawings, in which.

DETAILED DESCRIPTION OF THE INVENTION

Figure 1:
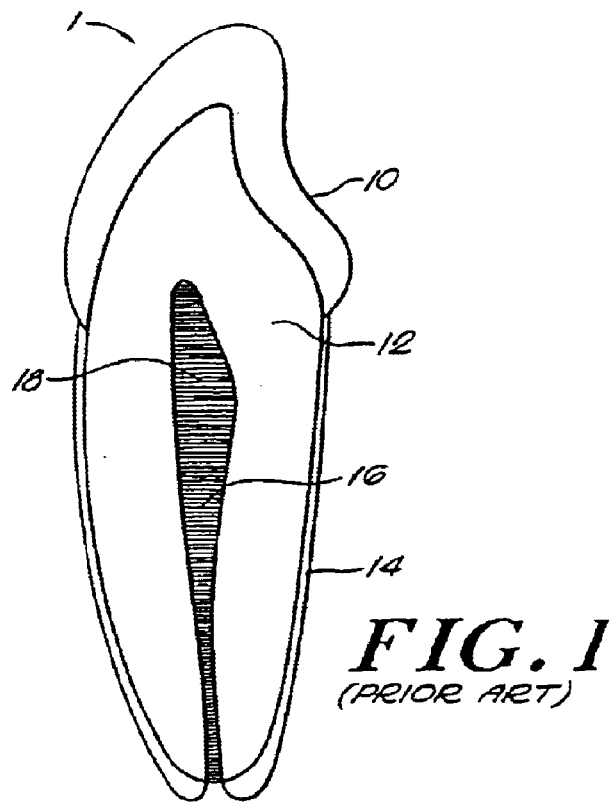
FIG. 1 is a cross-sectional view of a natural tooth.
Figures 2A, 2B:
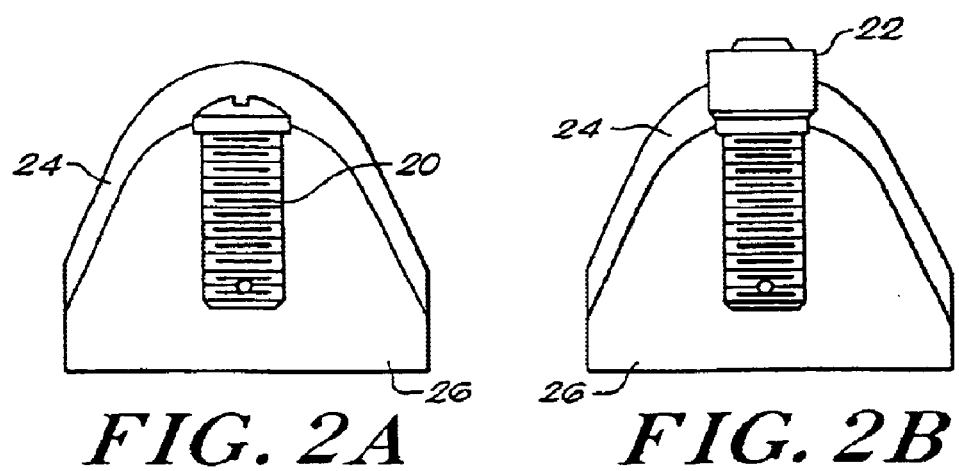
FIGS. 2a–d are cross-sectional views of a tooth including an implant, abutment, crown and restoration.
Figure 3:
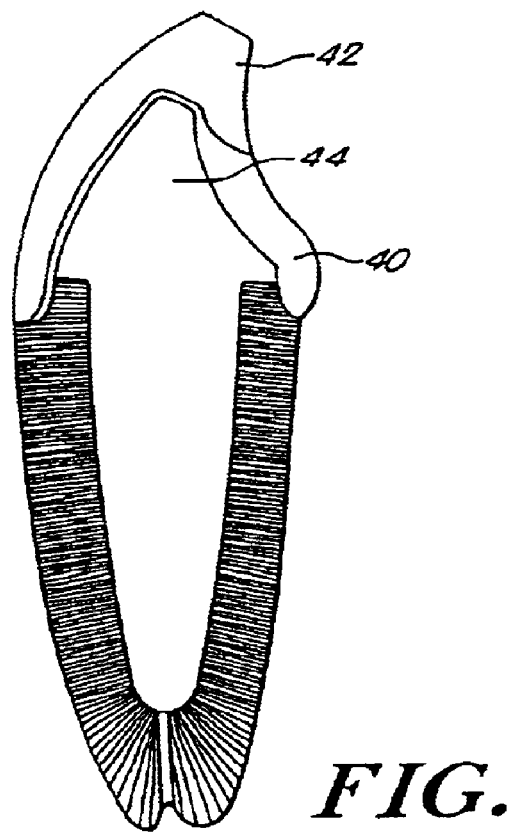
FIG. 3 is a cross-sectional view of a crown with a post and core manufactured by a process of the present invention.

As seen in FIGS. 2a and 2b, implant abutments 22 are screwed or cemented on top of the implant 20 which has been placed through the oral mucosa 24 and into the bone 26. They can take the form of a natural tooth to replace the missing tooth structure or may be only a core and post 40, as shown in FIG. 3, to act as a substructure restorative material which replaces the natural tooth. The implant abutment parts may be directly modified by the dentist to improve the fit and contour of the restoration. Presently, metal and Lexan plastic abutments are difficult to adjust in the clinic. The abutment cannot be easily bonded to by acrylic or composite resin to produce the final or temporary restoration.

Figure 2C:
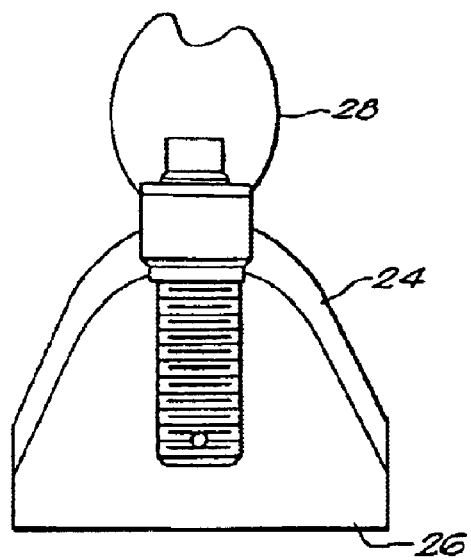
Figure 2D:
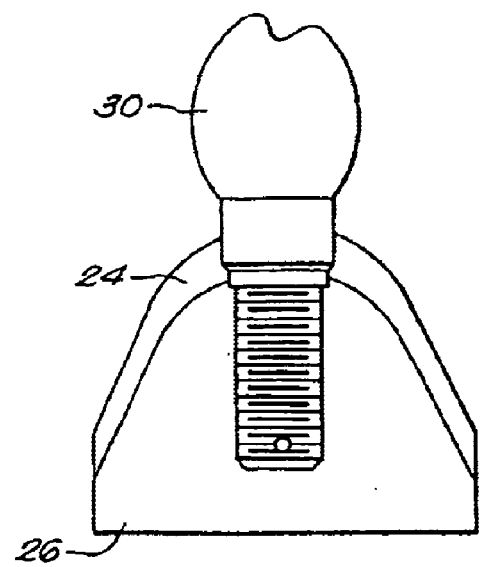

Endodontically treated teeth often require screwed retained crowns 28 or cemented crowns 30 as seen in FIGS. 2c and 2d. These teeth often have no remaining tooth structure above the gum line and require a post to be placed into the root canal and a core to be placed on top of the post.

The core and post 40 of FIG. 3 may also be manufactured as two separate pieces. Previously, these posts and cores were fabricated from metal, dense ceramic and composite resins. The tooth also includes a ceramic, metal or resin veneer 42 and metal coping 44. The veneer and coping combination may be formed as an all metal crown or an all ceramic crown.

A process of this invention may produce endodontic, orthodontic or restorative materials by the infusion of a dried ceramic with a monomer, glass, or metal alloy. Traditional composite materials possess discreet and isolated phases dispersed in a network. A material having an interpenetrating network involves the intertwining of two different types of materials. This intertwined network produces a single material with improved mechanical properties. This material may be produced by filling the pores of an open pore network of one material with a second material. When the pores of the first material are continuous throughout, capillary action may be used to draw the second material into the pores to create an interpenetrating network.

The infused material produces an improved restorative material which resists pull out of the filler because the ceramic particles are connected to each other and intertwined with the polymer (or metal alloy or glass or a combination of glass, metal or polymer). Wear may be reduced due to the high filler content, as well as the interpenetrating network of the polymer and ceramic filler. The material also may withstand flexing forces better than all-ceramic restorations because of the flexibility of the monomer (or metal alloy). During the process the monomer is infused and then cured in situ to create the polymer.

Specifically, a dry powder, such as feldspathic porcelain, a silica, alumina, a metal oxide, glass, etc. may be isopressed in a silicone mold. Alternatively, the sprayed dried powder may simply be pressed in a mold. The mold has the same shape as the final part. The powder is loaded into the silicone mold. The mold is then placed in a rubber/plastic bag and a vacuum of approximately $4\times10^{-2}$ torr is applied. The bag is sealed and the bag is then placed in a chamber containing a fluid, where the fluid is either water or oil. A piston is lowered into the chamber, sealing the chamber, and a pressure is applied. A pressure of approximately 1,000 psi to 50,000 psi is used to isostatically press the powder into the mold. After approximately five minutes, the pressure is release. After the part is removed from the chamber is fired at approximately 400–1200° C. to produce a porous ceramic network which is then silaned and resin infused. This method produces a more homogenous matrix.

Alternatively a wax or a polymeric binder such as polyethylene glycol or polyvinyl alcohol may be mixed with the dry powder. The mixture is either isopressed or injection molded to form the desired part. The binder is then burned out, the ceramic is sintered to produce a porous network and silane/resin infusion occurs.

The powder mixed with the binder may also be sprayed dried to produce regular spherical agglomerates. The powder is dispersed in a solution of the binder. It is heated to approximately 80–600° C. and forced through a nozzle having a diameter of 10–80 microns at a rate of 5–10 kg/hr to produce agglomerates of a specific diameter of about 10–100 microns, preferably around 50 microns, depending upon the starting size and spray drying parameters. The powder may be "dry-pressed" in a mold to form blocks, posts, abutments, or brackets. The resultant pressed part is then placed in a furnace to remove the binder. This method produces materials having superior mechanical properties.

After the dried material is removed from the mold, the dried alumina suspension is fired in a furnace at a temperature in a range of about 1000 to 1400° C. In order to avoid thermal shock, the dried material may be placed in a cold furnace and heated gradually to the firing temperature. For example, the temperature of the furnace may be raised at a rate of about 2 to 15° C. per minute until the desired firing temperature is reached.

The monomer infusion is accomplished by placing the samples and the monomer in a chamber, evacuating the chamber and then lowering the samples into the monomer where capillary action then draws the monomer into the porous ceramic matrix. This has nearly eliminated all infusion defects including point defects such as trapped air in the resin and allows one to easily scale up to a production level. The use of the vacuum chamber evacuates both the monomer and the air in the pores.

When vacuum infusing the specimens, the operator must first check on the monomer level to make sure that it is adequate for the size and number of samples in the basket. The monomer must be evacuated, i.e. degassed prior to the vacuum infusion process. If the monomer is new, the degassing takes approximately 2 hours. On the other hand, if the monomer supply is merely being supplemented, the evacuation process will only take approximately 30 minutes. Next the specimens are placed inside the pail. If there are only a few specimens in the basket, a weight made from materials such as lead should be placed in the basket. The pail is hooked to a string and a crank is turned to raise the pail into the upper section of the chamber.

The upper and lower chambers are placed in a sealing arrangement and the cover is put on top. The vent valve must be closed however the ballast valve should be slightly opened. The pressure is lowered until it remains at about $2 \times 10^{-1}$ torr (or less). The pressure should remain steady for at least about 15 minutes or as long as a few hours depending on the particular specimens and the resin. Then the vacuum is maintained at $4 \times 10^{-1}$ torr (or less) for at least 2 hours. The pail is then lowered into the monomer. The pressure will rise when the pail enters the resin. The pail remains in the resin for about 5 minutes. The vent valve is opened and the vacuum pump is stopped. The cover is removed and the specimens should be checked to insure that they are fully submerged and that the monomer is still liquid. The specimens are left submerged for at least 6 hours and may be submerged for up to 24 hours. The submersion time is dependent upon the porosity and the pore size in the specimens, the larger the pore size the shorter amount of time is required for submersion. The specimens are removed from the monomer and cured. The system should be run in a room with a temperature of approximately 19° C. and approximately 40% relative humidity.

The blocks of porous ceramic material are infused with a low fusing glass to a depth of approximately 2 mm. The remaining 10–15 mm is then secondarily infused with a monomer. This material has been used to fabricate dental restoration and implant abutments and post/cores. Also, the porous ceramic block may be infused first wit a metal and secondarily with a monomer or glass. In the case of implant abutments, the metal layer would be approximately 0.2–5.0 mm thick and would be located in the internal regions where the fixture screw contacts the abutment to provide added stress resistance to the torque placed on the screw. The outer layer would be glass or monomer infused to allow fabrication of a ceramic or monomer restoration. With respect to conventional (nonimplant) or machined crowns and bridges, the metal infused layer would be the same thickness and would be on the internal surface which is cemented to the tooth. The outer layer is then infused with monomer to fabricate the natural tooth contours or is glass infused to fabricate the rest of the restoration using a ceramic. It is possible that a glass/monomer combination would also be advantageous for orthodontic brackets or a post and core material.

The coronal portion of the fired material, e.g. high fusing ceramic matrixes such as zirconia, or alumina, or high fusing glasses such as lanthanum aluminosilicate, is then infused with a glass, such as lanthanum aluminosilicate glass or borosilicate glass, or a combination thereof, for about 0.5 to 1 hours at about 1100° C. This achieves a glass layer depth of about 1 to 2 mm. (Borosilicate and other low fusing glasses can be infused at approximately 550–800° C. Alternatively, the coronal portion of the fired material may be infused with a monomer, such as a light or heat-cured monomer. Such monomers, e.g., a mixture of triethylene glycol dimethacrylate (TEGDMA) and 2,2bis[4(2-hydroxy-3 methacryloyloxy-propyloxy)-phenyl]propane (BIS-GMA), may have a hardness in a range of about 40 to at least about 60 KHN and a flexural strength in a range of about 50 to 80 Mpa. For example, a heat-cured monomer may be cured in a low heat furnace at a temperature in a range of about 40 to 75° C. for about 24 hours. Moreover, camphoroquinone and benzoyl peroxide may be added to the monomer to effect light curing. Such a light-cured monomer may be cured with light in the visible blue spectrum for about 15 minutes.

Suitable monomers include acrylic monomers, such as hydroxy ethyl methacrylate (HEMA), TEGDMA, and BIS-GMA. Other suitable monomers include urethane dimethacrylate (UDM), biphenyldimethacrylate (BPDM), n-tolyglycine-glycidylmethacrylate (NTGE), polyethylene glycol dimethacrylate (PEG-DMA) and oligocarbonate dimethacrylic esters. Such monomers may be used alone, or two or more monomers may be used in combination. Further, colloidal silica may be added to the monomer to alter its index of refraction and mechanical properties. By altering the monomer's index of refraction, the color of the restoration may be adjusted. Moreover, acetone may be added to individual monomers (or monomer solutions) to alter their viscosity and control the rate of infusion.

The ceramic network also may be infused with a metal alloy to form a metal alloy layer. A suitable metal alloy has a melting point at least about 50° C. less than the ceramic network. For example, if the ceramic network includes alumina, a metal alloy including about 50% by weight of gold and about 5 to 10% by weight palladium or platinum, or both. Such a gold infused ceramic may be highly ductile, and appropriate adjustment of the ceramic network may produce a metal-ceramic material which retains many of the properties of the infused metal. These properties may include increased flexion and burnish ability and resistance to fracture. Typically the ceramic materials are infused with glass or metal, with metal then glass or with glass then metal, before being infused with silane followed by a monomer.

Excess glass, monomer, or metal alloy may be removed from the surface of the infused suspension, by using, for example, air abrasion or grinding. If air abrasion is used to remove the excess glass or monomer from a fired suspension which contains alumina particles, alumina particles with a mean diameter of about 50 $\mu$m are preferred as the abrasive. Such alumina particles are preferred as the abrasive because they minimize the contamination of the fired and infused suspension.

The advantages of the post and core material is that the material is translucent. Most conventional post and core materials are metal based and thus light transmission is blocked which negatively affect the ability to produce a restoration that mimics a natural tooth. Even ceramic posts are opaque. Presently, many restorations are fabricated from all ceramic materials which are translucent. A non-translucent post and core eliminates the aesthetic advantage of an all ceramic restoration. Additionally the material is easily cemented into the tooth and is also easily adjusted by the dentist working with the product. The material can be produced in a variety of shades to match the shade used to fabricate the overlying crown.

The materials have a high strength and toughness but are not as brittle as ceramics and they also tend to protect the root by failing at the gum line. Conventional metal posts and ceramic posts tend to cause a roof fracture when they break. The tooth then has to be extracted. If the material fails at the gum line, the root is spared and the tooth can be saved for retreatment.

There are many advantages to using this material for orthodontic brackets, specifically they can be highly translucent and thus almost transparent bracket. The bracket will tend to blend in with teeth and will be more aesthetic than current metal and ceramic brackets. The bracket has a greater toughness than existing materials and may be more resistant to failure than ceramic brackets. The ceramic brackets are used as an aesthetic alternative to metal but suffer from failure at the wings due to their brittle nature. The brackets also have less friction that ceramic brackets. One of the problems with the ceramic brackets is high friction with the wires thus prolonging treatment.

There are also many advantages of using the material for an implant abutment including the aesthetics, the ease of adjustment and decreased stress transfer. Conventional implant abutments must be custom made or custom adjusted in the laboratory. Also the prior metal abutments may transfer stress directly to the bone leading to accelerated bone resorption. The resin ceramic abutments may act as a shock absorber.

A direct filling material would be used by the dentist and placed directly on the tooth to rebuild missing tooth structure. This is commonly called a composite resin. Current composite resins are based on filling a fluid monomer with micron/submicron glass or ceramic particles and then curing the monomer. These particles are not connected. This leads to problems with wear as the particles pull out and leave behind the relatively soft resin. Particle connection to the resin matrix is a significant problem. Also it is difficult to compress these materials into small spaces which often results in gaps between the filling material and the tooth, leading to recurrent decay and sensitivity.

The proposed new composite polymer material is based on using interconnecting infused ceramic blocks to produce a powder with particle sizes approximately 10–100 microns. The blocks may be cryogenically milled or hammer milled to produce the starting powder. The particles would actually be interconnected ceramic and polymeric units. The particles may be silane treated before mixing with monomer to improve wetting of the particles with the monomer and bonding of the particles. The silane treatment includes infusing the blocks with a silane solution for 24 hours before heating them at approximately 100° C. for about 1 hour before monomer infusion. The preferred silane solution is a 1 wt % 3-methaciyloxpropyltrimethoxysilane in a 50/50 mixture of ethanol and-water. The pH is adjusted with acetic acid to a value of about 4.

The particles would then be mixed with a light or heat curing agent (TEGDMA/UDM; BIS-GMA/UDM) similar to that described in the parent patent. This produces a viscous paste which can be directly applied to the tooth and cured. Subsequent adjustment and finishing procedures such as polishing allows the placement of the restoration in a single visit. Additional particles consisting of micron/submicron silica or ceramic may be added to the mixture to alter viscosity and mechanical properties. The total loading of the resin with filler will be in the range of 60–80% by volume. The advantages of this composite resin is two fold. First the filler material consists of interconnected polymer-ceramic particle which improves bonding of the filler to the polymer matrix and should result in decreased wear and improved mechanical properties. And second, the ability to compress this material is improved due to the interconnected filler units.

Other embodiments of the invention will be apparent to those skilled in the art from a consideration of this specification or practice of the invention disclosed herein. Although a detailed description and examples of the present invention has been provided above, it is to be understood these are exemplary and that the scope of the invention is not be limited thereby, but is to be determined by the claims which follow.

What is now claimed is:

1. A ceramic network composite for endodontic, orthodontic or implant dental restorations which comprises:
at least one and another layer, the one layer being infused with a metal to form an interpenetrating network composite and the other layer being infused with a composition selected from the group consisting essentially of glass or monomer to form an interpenetrating composite network, at least one of the physical properties of hardness, flexural strength and elastic modulus of one layer being distinct from that of the other layer.

2. The network composite of claim 1 wherein the ceramic is selected from the group consisting of feldspathic porcelain, a silica, alumina, or glass.

3. The network composite of claim 1 wherein the metal is selected from the group consisting of gold, platinum, or palladium.

4. The network composite of claim 1 wherein the monomer is selected from the group consisting essentially of hydroxy ethyl methacrylate; triethylene glycol dimethacrylate; 2,2bis [4(2-hydroxy-3methacryloyloxy-propyloxy)-phenyl]propane; urethane dimethylacrylate, biphenyldimethacrylate; n-tolyglycine-glycidylmethacrylate; polyethylene glycol dimethacrylate; or oligocarbonate dimethacrylic esters.

5. A ceramic network composite for endodontic, orthodontic or implant dental restorations which comprises:
at least one and another layer, the one layer being infused with a glass to form an interpenetrating network composite and the other layer being infused with a monomer to form an interpenetrating composite network, at least one of the physical properties of hardness, flexural strength and elastic modulus of one layer being distinct from that of the other layer.

6. The network composite of claim 5 wherein the monomer is selected from the group consisting of hydroxy ethyl methacrylate; triethylene glycol dimethacrylate; 2,2bis [4(2-hydroxy-3 methacryloyloxy-propyloxy)-phenyl]propane; urethane dimethylacrylate, biphenyldimethacrylate; n-tolyglycine-glycidylmethacrylate; polyethylene glycol dimethacrylate; or oligocarbonate dimethacrylic esters.

* * * * *